United States Patent
Marrouche et al.

(10) Patent No.: US 10,004,425 B2
(45) Date of Patent: *Jun. 26, 2018

(54) PATIENT SPECIFIC SCAN PARAMETERS FOR MRI SCANNING

(71) Applicant: UNIVERSITY OF UTAH RESEARCH FOUNDATION, Salt Lake City, UT (US)

(72) Inventors: Nassir F. Marrouche, Salt Lake City, UT (US); Evgueni G. Kholmovski, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/658,741

(22) Filed: Jul. 25, 2017

(65) Prior Publication Data

US 2017/0332940 A1 Nov. 23, 2017

Related U.S. Application Data

(63) Continuation of application No. 14/355,201, filed as application No. PCT/US2012/062616 on Oct. 30, 2012, now Pat. No. 9,713,436.

(Continued)

(51) Int. Cl.
*A61B 5/055* (2006.01)
*G01R 33/50* (2006.01)
(Continued)

(52) U.S. Cl.
CPC .............. *A61B 5/055* (2013.01); *A61B 5/046* (2013.01); *A61B 5/0452* (2013.01);
(Continued)

(58) Field of Classification Search
CPC ....... A61B 5/0452; A61B 5/046; A61B 5/055; G01R 33/4818; G01R 33/50;
(Continued)

(56) References Cited

U.S. PATENT DOCUMENTS

| 5,687,737 A | 11/1997 | Branham et al. |
| 5,776,063 A | 7/1998 | Dittrich et al. |

(Continued)

FOREIGN PATENT DOCUMENTS

| JP | 2001-149340 | 6/2001 |
| JP | 2005-185732 | 7/2005 |

(Continued)

OTHER PUBLICATIONS

"Moderate Poster MPO1-1 ED—Fogel Richard", Heart Rhythm, Elsevier, US, vol. 7, No. 5, May 1, 2010 (May 1, 2010), pp. 5446-5458.

(Continued)

*Primary Examiner* — Ruth S Smith
(74) *Attorney, Agent, or Firm* — Michael Best & Friedrich LLP

(57) ABSTRACT

A method of optimizing scan parameters for LGE-MRI. At least one cardiac MRI TI scout scan is performed by applying an inversion pulse every predetermined heartbeat of a patient. An initial value of an inversion time $TI_{initial}$ is determined by assessing a set of images generated from the scout scan. A first multiple of a duration between successive indicia of ventricular depolarization is selected, and a relaxation time T1 is determined based on the initial value $T_{initial}$ and the first multiple of duration. An optimized inversion time $TI_{optimal}$ for LGE-MRI is determined based on the relaxation time T1 and a second multiple of a duration between successive indicia of ventricular depolarization. A correction factor is determined based on the optimized inversion time $TI_{optimal}$ from the initial value of the inversion time $TI_{initial}$.

26 Claims, 4 Drawing Sheets

Related U.S. Application Data

(60) Provisional application No. 61/553,836, filed on Oct. 31, 2011.

(51) Int. Cl.
*A61B 5/046* (2006.01)
*A61B 5/0452* (2006.01)
*G01R 33/48* (2006.01)
*G01R 33/56* (2006.01)
*G01R 33/567* (2006.01)
*G01R 33/54* (2006.01)

(52) U.S. Cl.
CPC ......... *G01R 33/4818* (2013.01); *G01R 33/50* (2013.01); *G01R 33/543* (2013.01); *G01R 33/5601* (2013.01); *G01R 33/5602* (2013.01); *G01R 33/5673* (2013.01); *G01R 33/546* (2013.01)

(58) Field of Classification Search
CPC .......................... G01R 33/543; G01R 33/546; G01R 33/5601; G01R 33/5602; G01R 33/5673
See application file for complete search history.

(56) References Cited

U.S. PATENT DOCUMENTS

| | | | |
|---|---|---|---|
| 6,064,906 | A | 5/2000 | Langberg et al. |
| 9,713,436 | B2* | 7/2017 | Marrouche ............ A61B 5/055 |
| 2002/0049384 | A1 | 4/2002 | Davidson et al. |
| 2002/0072490 | A1 | 6/2002 | Kapeller-Libermann et al. |
| 2003/0042905 | A1 | 3/2003 | Miyazaki et al. |
| 2003/0176782 | A1 | 9/2003 | Graessner |
| 2004/0167510 | A1 | 8/2004 | Feld et al. |
| 2005/0242973 | A1 | 11/2005 | Liebl et al. |
| 2005/0245812 | A1 | 11/2005 | Kim et al. |
| 2007/0236491 | A1 | 10/2007 | Hundley et al. |
| 2008/0031506 | A1 | 2/2008 | Agatheeswaran et al. |
| 2008/0214931 | A1 | 9/2008 | Dickfeld |
| 2008/0214945 | A1 | 9/2008 | Koertge et al. |
| 2008/0242973 | A1 | 10/2008 | Warmuth |
| 2009/0182287 | A1 | 7/2009 | Kassab |
| 2010/0160765 | A1 | 6/2010 | Marrouche et al. |
| 2010/0160768 | A1 | 6/2010 | Marrouche et al. |
| 2010/0292561 | A1 | 11/2010 | Greiser |
| 2010/0298694 | A1 | 11/2010 | Marrouche et al. |
| 2011/0009861 | A1 | 1/2011 | Mukherjee et al. |
| 2014/0378822 | A1 | 12/2014 | Marrouche et al. |

FOREIGN PATENT DOCUMENTS

| | | |
|---|---|---|
| WO | WO 2010/075450 | 7/2010 |
| WO | WO 2010/075468 | 7/2010 |
| WO | WO 2011/146779 | 11/2011 |

OTHER PUBLICATIONS

"Sixteenth Meeting of the European Neurological Society May 27-31, 2006, Lausanne, Switzerland; Symposia and Free Communications", Journal of Neurology, Steinkopff-Verlag, DA, vol. 253, No. 2, May 1, 2006, pp. ii1-ii170.
Aime-Sempe, C. et al., "Correlation between Left Atrial Structural Remodeling with Persistence and Recurrence in Patients with Atrial Fibrillation" AB30-2 (May 14, 2008) <http://www.abstracts2view.com/hrs/view.php?nu+HRS08L_5375>.
Aime-Sempe, C. et al., "Myocardial cell death in fibrillating and dilated human right atria," J. Am Coll Cardiol, 1999, 34:1577-86.
Akoum NW, Daccarett M, McGann CJ, Segerson N, Vergara G, Kuppahally S, et al. "Atrial fibrosis helps select the appropriate patient and strategy in catheter ablation of atrial fibrillation: A DE-MRI guided approach," J Cardiovasc Electrophys 2011;22:16-22.
Akoum, N. et al., "Correlation between Left Atrial Structural Remodeling with Persistence and Recurrence in Patients with Atrial Fibrillation" AB30-2 (May 14, 2008) <http://www.abstracts2view.com/hrs/view.php?nu+HRS08L_5375>.
Allessie M, Ausma J, Schotten U. Electrical, contractile and structural remodeling during atrial fibrillation. Cardiovasc Res 2002;54:230-246.
Anne et al., "Matrix metalloproteinases and atrial remodeling inpatients with mitral valve disease and atrial fibrillation" Cardiovascular Research, 2005, 655-666, vol. 67.
Aronow, W. S. et al., "Risk factors for new thromboembolic stroke inpatients > or = 62 years of age with chronic atrial fibrillation" Am J Cardiol 1998, 82:119-21.
Aronow, W. S. et al., "Risk factors for thromboembolic stroke in elderly patients with chronic atrial fibrillation" Am J Cardiol 1989, 63:366-7.
Atrial Fibrillation Investigators. Risk factors for stroke and efficacy of antithrombotic therapy in atrial fibrillation. Arch Intern Med 1994, 154:1449-57.
Badger TJ, Daccarett M, Akoum NW, Adjei-Poku YA, Burgon NS, Haslam TS, et al. Evaluation of left atrial lesions after initial and repeat atrial fibrillation ablation: Lessons learned from delayed-enhancement MRI in repeat ablation procedures. Circulation: Arrhythm and Electrophysiol 2010;3:249-259.
Badger, T. J. et al., "Catheter Ablation of Atrial Fibrillation Abstract 2753: The Relationship Between Pulmonary Vein Antrum Scarring Following Atrial Fibrillation Ablation and Procedural Success: Does Pulmonary vein Isolation Matter?" Circulation 2008, 118:S_771.
Badger, T. J. et al., "Temporal left atrial lesion formation after ablation of atrial fibrillation" Heart Rhythm 2009, 6:161-8.
Berruezo et al., "Pre-Procedural Predicators of Atrial Fibrillation Recurrence After Circumferential Pulmonary vein Ablation" European Heart Journal, 2007, vol. 28, pp. 836-841.
Cabin, H. S. et al., "Risk for systemic embolization of atrial fibrillation without mitral stenosis", Am J Cardiol 1990, 65:1112-6.
Calo, L. et al., "Left atrial ablation versus biatrial ablation for persistent and permanent atrial fibrillation: a prosprective randomized study" J Am Coll Cardiol 2006, 47:2504-12.
Caplan, L. R. et al., "Atrial size, atrial fibrillation, and stroke" Ann Neurol 1986, 19:158-61.
Chugh, A. et al., "Prevalence, mechanisms, and clinical significance of macroreentrant atrial tachycardia during and following left atrial ablation for atrial fibrillation", Heart Rhythm 2005, 2:464-71.
Corbalan, R. et al., "Risk factors for systemic embolism in patients with paroxysmal atrial fibrillation", Am Heart J 1992, 124:149-53.
Corradi D, Callegari S, Benussi S, et al. Myocyte changes and their left atrial distribution inpatients with chronic atrial fibrillation related to mitral valve disease. Hum Pathol 2005;36:1080-1089.
Daccarett M, Badger TJ, Akoum NW, Burgon NS, Mahnkopf C, Vergara G, et al. Association of left atrial structural remodeling detected by delayed-enhancement MRI and the risk of stroke inpatients with atrial fibrillation. J Am Coll Cardiol 2011;57:831-838.
De Cobelli, F. et al., "Delayed gadolinium-enhanced cardiac magnetic resonance inpatients with chronic myocarditis presenting with heart failure or recurrent arrhythmias", J Am Coll Cardiol 2006, 47:1649-54.
Dearborn, J. L. et al., "Perception of risk and knowledge of risk factors in women at high risk for stroke", Stroke 2009, 40:1181-6.
Dickfield, T. et al., "Characterization of radiofrequency ablation lesions with gadolinium-enhanced cardiovascular magnetic resonance imaging" J Am Coll Cardiol 2006, 47:370-8.
Echocardiographic Predictors of Stroke in Patients With Atrial Fibrillation. A prospective study of 1,066 Patients from 3 clinical trials, Arch Intern Med 1998, 158:1316-20.
Ezekowitz et al., "Echocardiographic Predictors of Stroke in Patients With Atrial Fibrillation" Arch Intern Med., 1998, 1316-1320, vol. 158.
Fang et al., "Comparison of Risk Stratification Schemes to Predict Thromboembolism in People With Nonvalvular Atrial Fibrillation" J. of the American College of Cardiology, 2008, 810-815, vol. 51, No. 8.

(56) References Cited

OTHER PUBLICATIONS

Fatema, K. et al., "Increased left atrial vol. index: potent biomarker for first-ever ischemic stroke" Mayo Clin Proc 2008, 83:1107-15.
Fuster V RL, Cannom DS, Crijns HJ, Curtis AB, Ellenbogen KA, Halperin JL, Le Heuzey JY, Kay GN, Lowe JE, Olsson SB, Prystowsky EN, Tamargo JL, Wann S, Smith SC Jr, Jacobs AK, Adams CD, Anderson JL, Antman EM, Halperin JL, Hunt SA, Nishimura R, Ornato JP, Page RL, Riegel B, Priori SG, Blanc JJ, Budaj A, Camm AJ, Dean V, Deckers JW, Despres C, Dickstein K, Lekakis J, McGregor K, Metra M, Morais J, Osterspey A, Tamargo JL, Zamorano JL; American College of Cardiology; American Heart Association Task Force; European Society of Cardiology Committee for Practice Guidelines; European Heart Rhythm Association; Heart Rhythm Society. ACC/AHA/ESC 2006 Guidelines for the Management of Patients with Atrial Fibrillation: a report of the American College of Cardiology/American Heart Association Task Force on Practice Guidelines and the European Society of Cardiology Committee for Practice Guidelines (Writing Committee to Revise the 2001 Guidelines for the Management of Patients With Atrial Fibrillation): developed in collaboration with the European Heart Rhythm Association and the Heart Rhythm Society. Circulation 2007;114:98.
Gage et al., "Selecting Patients With Atrial Fibrillation for Anticoagulation: Stroke Risk Stratification in Patients Taking Aspirin" Circulation, 2004, 2287-2292, vol. 110.
Gage et al., "Validation of Clinical Classification Schemes for Predicting Stroke: Results From the National Registry of Atrial Fibrillation" J American Medical Association, 2001, 2864-2870, vol. 285, No. 22.
Gage, B. F. et al., "Cost-effectiveness of preference-based antithrombotic therapy for patients with nonvalvular atrial fibrillation" Stroke 1998, 29:1083-91.
Gaita, F. et al., "Linear cryoablation of the left atrium versus pulmonary vein cryoisolation in patients with permanent atrial fibrillation and valvular heart disease: correlation of electroanatomic mapping and long-term clinical results" Circulation 2005, 111:136-42.
Gerstenfeld, E. P et al., "Utility of exit block for identifying electrical isolation of the pulmonary veins", J Cardiovasc Electrophysiol 2002, 13:971-9.
Goldman, M. E. et al., "Transesophageal echocardiographic correlates of a clinical risk of thromboembolism in nonvascular atrial fibrillation. Reduced flow velocity in the left atrial appendage", J Am Soc Echo 1999, 12:1080-7.
Haissaguerre, M. et al., "Catheter ablation of long-lasting persistent atrial fibrillation: clinical outcome and mechanisms of subsequent arrythmias" J Cardiovasc Electrophysiol 2005, 16:1138-47.
Haissaguerre, M. et al., "Catheter ablation of long-lasting persistent atrial fibrillation: clinical structures for termination" J Cardiovasc Electrophysiol 2005, 16:1125-37.
Haissaguerre, M. et al., "Spontaneous initiation of atrial fibrillation by ectopic beats originating in the pulmonary veins", N Engl J Med 1998, 339:659-66.
Halperin et al., "Damage Assessment after Ablation", Journal of the American College of Cardiology, 2008, pp. 1272-1273, vol. 52, No. 15, Elsevier Inc.
Hart, "Independent predictors of stroke inpatients with atrial fibrillation: A systematic review" Neurology, 2007, 546-554, vol. 69.
Hart, R. G. et al., "Antithrombotic therapy to prevent stroke inpatients with atrial fibrillation: a meta-analysis", Ann Intern Med 1999, 131:492-501.
Hsu, L. Y. et al., "Quantitative myocardial infarction on delayed enhancement MRI. Part I: animal validation of an automated feature analysis and combined thresholding infarct sizing algorithm", J Magn Reson Imaging 2006, 23:298-308.
Hsu, L. Y. et al., "Quantitative myocardial infarction on delayed enhancement MRI. Part II: clinical application of an automated feature analysis and combined thresholding infarct sizing algorithm", J Magn Reson Imaging 2006, 23:309-14.
Karch, M. R. et al., "Freedom from atrial tachyarrhythmias after catheter ablation of atrial fibrillation: a randomized comparison between 2 current ablation strategies", Circulation 2005, 111:2875-80.
Kholmovski et al., "Calculation of Optimal TI Value for 3D LGE-MRI of the Let't Atrium," Proc. Intl. Soc. Mag. Reson Med. 21 (2013) p. 4562.
Kim, R. J. et al., "Relationship of MRI delayed contrast enhancement to irreversible injury, infarct age, and contractile function", Circulation 1999, 100:1992-2002.
Kim, R. J., "The use of contrast-enhanced magnetic resonance imaging to identify reversible myocardial dysfunction" N Engl J Med 2000, 343:1445-53.
Kistler, P. M. et al., "Electrophysiologic and anatomic characterization of sites resistant to electrical isolation during circumferential pulmonary vein ablation for atrial fibrillation: a prospective study", J Cardiovasc Electrophysiol 2007, 18:1282-8.
Kistler, P. M. et al., "The impact of CT image integration into an electroanatomic mapping system on clinical outcomes of catheter ablation of atrial fibrillation", J cardiovasc Electropysiol 2006, 17:1093-101.
Klein, C. et al., "Assessment of myocardial viability with contrast-enhanced magnetic resonance imaging: comparison with positron emission tomography", Circulation 2002, 105:162-7.
Knuesel, P. R. et al., "Characterization of dysfunctional myocardium by positron emission tomograpgy and magnetic resonance: relation to functional outcome after revascularization", Circulation 2003, 108:1095-100.
Laissy, J. P. et al., "Differentiating acute myocardial infarction from myocarditis: diagnostic value of early- and delayed-perfusion cardiac MR imaging", Radiology 2005, 237:75-82.
Lardo, A. C. et al., "Visualization and temporal/spatial characterization of cardiac radiofrequency ablation lesions using magnetic resonance imaging", Circulation 2000, 102:698-705.
Levitt et al., "NMR Population Inversion Using a Composite Pulse," Journal of Magnetic Resonance 33, 473-476 (1979).
Lewsey, J. D. et al., "Sex differences in incidence, mortality, and survival in individuals with stroke in Scotland, 1986 to 2005", Stroke 2009, 40:1038-43.
Li D, Fareh S, Leung T, Nattel S. Promotion of atrial fibrillation by heart failure in dogs: Atrial remodeling of a different sort. Circulation 1999;100:87-95.
Li, D. et al., "Effects of angiotensin-converting enzyme inhibition on the development of the atrial fibrillation substrate in dogs with ventricular tachypacing-induced congestive heart failure", Circulation 2001, 104:2608-14.
Lip et al., "Additive Role of Plasma von Willebrand Factor Levels to Clinical Factors for Risk Stratification of Patients With Atrial Fibrillation" Stroke, 2006, 2294-2300 and 2444, vol. 37.
Look DC, Locker DR. Time saving in measurement of NMR and EPR relaxation times. Rev Sci Instrum 1970;41:250-251.
Mahrholdt, H. et al., "Cardiovascular magnetic resonance assessment of human myocarditis: a comparison to histology and molecular pathology", Circulation 2004, 109:1250-8.
Marrouche, N. F. et al., "Circular mapping and ablation of the pulmonary vein for treatment of atrial fibrillation impact of different catheter technologies," J Am Coll Cardiol 2002, 40:464-74.
Marrouche, N. F. et al., "Phase-array intracardiac ecocardiography monotoring during pulmonary vein isolation inpatients inpatients with atrial fibrillation: impact on outcome and complications", Ciculation 2003, 107:2710-6.
McGann CJ, Kholmovski EG, Oakes RS, Blauer JJE, Daccarett M, Segerson N, et al. New magnetic resonance imaging-based method for defining the extent of left atrial wall injury after the ablation of atrial fibrillation. J Am Coll Cardiol 2008;52:1263-1271.
Menon, S. C. et al., "Critical factors determining access to acute stroke care", Neurology 1998, 51:427-32.
Nademanee, K. et al., "A new approach for catheter ablation of atrial fibrillation mapping of the electrophysiologic substrate", J Am Coll Cardiol 2004, 43:2044-53.
Naganawa et al., "Estimation of Gadolinium-induced T1-shortening with Measurement of Simple Signal Intensity Ratio between the

(56) References Cited

OTHER PUBLICATIONS

Cochlea and Brain Parenchyma on 3D-Flair: Correlation with T1 Measurement by TI Scout Sequence," Magn Reson Med Sci, vol. 9, No. 1, pp. 17-22, 2010.

Natale, A. et al., "Prospective randomized comparison of antiarrhythmic therapy versus first-line radiofrequency ablation inpatients with atrial flutter", J Am Coll Cardiol 2000, 35:1898-904.

Oakes RS, Badger TJ, Kholmovski EG, et al. Detection and quantification of left atrial structural remodeling with delayed-enhancement magnetic resonance imaging in patients with atrial fibrillation. Circulation. 2009;119:1758-1767.

Oh, S. et al., "Avoiding microbubbles formation during radiofrequency left atrial ablation versus continuous microbubbules formation and standard radiofrequency ablation protocols: comparison of energy profiles and chronic lesion characteristics" J Cardiovasc Electrophysiol 2006, 17:72-7.

Okuyama et al., "Usefulness of Intensity Varation in the Left Atrial Appendage With Contrast Echocardiolography to Predict Ischemic Stroke Recurrence in Patients With Atrial Fibrillation", The American Journal of Cardiology, 2008, vol. 101, pp. 1630-1637.

Olshansky et al., "Fibrillation recurrence or Stroke?: Results From the Atrial Fibrillation Are Transthoracic Echocardiographic Parameters Associate With Atrial Follow-Up Investigation of Rhythm Management (AFFIRM) Study", Journal of the American College of Cardiology, 2005, vol. 45, No. 12, pp. 2026-2033.

Oral, H. et al., "Circumferential pulmonary-vein ablation for chronic atrial fibrillation" N Engl J Med 2006, 354:934-41.

Oshinski, J. N. et al., "Quantitative prediction of improvement in cardiac function after revascularization with MR imaging and modeling: initial results", Radiology 2001, 221:515-22.

Ouyang, F. et al., "Electrophysiological findings during ablation of persistent atrial fibrillation with electroanatomic mapping and double Lasso catheter technique", Circulation 2005, 112:3038-48.

Ouyang, F. et al., "Recovered pulmonary vein conduction as a dominant factor for recurrent atrial tachyarrhythmias after complete circular isolation of the pulmonary veins: lessons from double Lasso technique", Circulation 2005, 111:127-35.

Pan et al., "Aging Dilates Atrium and Pulmonary Veins Implications for the Genesis of Atrial Fibrillation" Chest, 2008, 190-196, vol. 133.

Parkash et al., "The Association of Left Atrial Size and Occurrence of Atrial Fibrillation: A Prospective cohort Study From the Canadian Registry of a Atrial Fibrillation", American Heart Journal, 2004, vol. 148, pp. 649-654.

Peters DC, Wylie JV, Hauser TH, Kissinger KV, Botnar RM, Essebag V, et al. Detection of pulmonary vein and left atrial scar after catheter ablation with three-dimensional navigator-gated delayed enhancement MR imaging: Initial experience. Radiology 2007;243:690-695.

Peters, et al., "Recurrence of Atrial Fibrillation Following RF Ablation Correlates with the Extent of Post-procedural Left Atrial Scarring on Delayed-Enhancement CMR", Circulation, 2007, pp. 1-3, American Heart Association, Abstract 3371, <http://circ.ahajournals.org/cgi/content/meeting_abstract/116/16_MettingAbstracts/II_760-d>.

Petersen, P. et al., "Risk factors for thromboembolic complications in chronic atrial fibrillation. The Copenhagen AFASAK study", Arch Intern Med 1990, 150:819-21.

Pritchett, A. M. et al., "Left atrial volume as an index of left atrial size: a population-based study", J Am Coll Cardiol 2003, 41:1036-43.

Rochitte, C. E. et al., "The emerging role of MRI in the diagnosis and management of cardiomyopathies", Curr Cardiol Rep 2006, 8:44-52.

Sanders, P. et al., "Electrical remodeling of the atria in congestive heart failure: electrophysiological and electronatomic mapping in humans", Circulation 2003, 108:1461-8.

Sauer, W. H. et al., "Clinical predictors and outcomes associated with accute return of pulmonary vein conduction during pulmonary vein isolation for treatment of atrial fibrillation", Heart Rhythm 2006, 3:1024-8.

Schoonderwoerd BA, Van Gelder IC, Van Veldhuisen DJ, Vanden Berg MP, Crijns HJ. Electrical and structural remodeling: Role in the genesis and maintenance of atrial fibrillation. Prog Cardiovasc Dis 2005;48:153-168.

Segerson NM, Daccarett M, Badger TJ, Shabaan A, Akoum N, Fish EN et al. Magnetic resonance imaging-confirmed ablative debulking of the left atrial posterior wall and septum for treatment of persistent atrial fibrillation Rationale and initial experience. J Cardiovasc Electrophysiol 2010;21:126-132.

Seneviratne, B. I. et al., "Nonvalvular atrial fibrillation associated with cardioembolic stroke: the role of hypertensive heart disease", Aust N Z J Med 1990, 20:127-34.

Shin, S. H. et al., "Left Atrial Volume Is a Predictor of Atrial Fibrillation Recurrence After Catheter Ablation", Journal of the American Society of Echocardiography, 2008, vol. 21, issue 6, pp. 697-702.

Sievers, B. et al., "Cardiovascular magnetic resonance of iatrogenic ventricular scarring due to catheter ablation for left ventricular tachycardia", Int J Cardiol 2003, 91:249-50.

Spach, M. et al., "The functional role of structural complexities in the propagation of depolarization in the atrium of the dog. Cardiac conduction disturbances due to discontinuities of effective axial resistivity", Circ Res 1982, 50:175-91.

Stollberger et al., "Transesophageal Echocardiography to Assess Embolic Risk in Patients with Atrial Fibrillation" Annals of Internal Medicine, 1998, 630-638, vol. 128.

Suranyi et al., "Equilibrium signal intensity mapping an MRI method for fast mapping of longitudinal relaxation rates and for image enhancement" Magnetic Resonance Imaging 25 (2007) 641-651.

Tanaka et al., "Spatial Distribution of Fibrosis Governs Fibrillation Wave Dynamic in the Posterior Left Atrium During Heart Failure" Circulation research, 2007, 839-847 and online supplement pp. 1-33, vol. 101.

The SPAF III Writing Committee for the Stroke Prevention in Atrial Fibrillation Investigators. Patients with nonvalvular atrial fibrillation at low risk of stroke during treatment with aspirin: Stroke Prevention in Atrial Fibrillation III study, JAMA 1998, 279:1273-7.

The Stroke Prevention in Atrial Fibrillation Investigators. Predictors of thromboembolism in atrial fibrillation: II. Echocardiographic features of patients at risk Ann Intern Med 1992, 116:6-12.

The Stroke Risk in Atrial Fibrillation Working Group. Independent predictors of stroke inpatients with atrial fibrillation a systematic review, Neurology 2007, 69:546-54.

Verma, A. et al, "Response of atrial fibrillation to pulmonary vein antrum isolation is directly related to resumption and delay of pulmonary vein conduction", Circulation 2005, 112:627-35.

Vijayakumar et al., "Contrast Optimization for LGE imaging of Left Atrium," Proceedings of the International Society for Magnetic Resonance in Medicine, ISMRM, 18th Scientific Meeting and Exhibition, Stockholm, Sweden, May 1-7, 2010.

Wazni, O. M. et al., "Radiofrequency ablation vs antiarrhythmic drugs as first-line treatment of symptomatic atrial fibrillation a randomized trial" JAMA 2005, 293:2634-40.

Wijffels MC, Kirchhof CJ, Dorland R, Allessie MA. Atrial fibrillation begets atrial fibrillation. A study in awake chronically instrumented goats. Circulation 1995;92:1954-1968.

Willems, S. et al., "Substrate modification combined with pulmonary vein isolation improves outcome of catheter ablation in patients with persistent atrial fibrillation: a prospective randomized comparison" Eur Heart J 2006, 27:2871-8.

Wolf, P. A. et al., "Atrial fibrillation: a major contributor to stroke in the elderly. The Framingham Study", Arch Intern Med 1987, 147:1561-4.

Wongcharoen, W. et al., "Effects of aging and ouabain on left atrial arrhythmogenicity", J Cardiovasc Electrophysiol 2007, 18:526-31.

Zabalgoitia et al., "Transesophageal echocardiographic correlates of clinical risk of thromboembolism in nonvalvular atrial fibrillation.

(56) References Cited

OTHER PUBLICATIONS

Stroke Prevention in Atrial Fibrillation III Investigators" J. of the American College of Cardiology, 1998, 1622-1626, vol. 31.
Australian Patent Office Action for Application No. 2012332703 dated Aug. 5, 2016 (3 pages).
European Patent Office Action for Application No. 09835812.0 dated Jan. 31, 2014 (6 pages).
European Patent Office Extended Search Report for Application No. 09835801.3 dated Jul. 2, 2014 (13 pages).
European Patent Office Extended Search Report for Application No. 12846149.8 dated May 29, 2015 (10 pages).
Extended European Patent Office Search Report for Application No. 11784282 dated Sep. 21, 2015 (9 pages).
International Search Report and Written Opinion for Application No. PCT/US2009/069306 dated Jul. 21, 2010 (6 pages).
International Search Report and Written Opinion for Application No. PCT/US2009/069330 dated Jul. 21, 2010 (6 pages).
International Search Report and Written Opinion for Application No. PCT/US2011/037251 dated Aug. 24, 2011 (8 pages).
International Search Report and Written Opinion for Application No. PCT/US2012/062616 dated Feb. 7, 2013 (9 pages).
United States Patent Office Action for U.S. Appl. No. 12/344,164 dated Dec. 5, 2014 (15 pages).
United States Patent Office Action for U.S. Appl. No. 12/344,164 dated Oct. 19, 2015 (17 pages).
United States Patent Office Action for U.S. Appl. No. 12/344,164 dated Sep. 15, 2016 (21 pages).
United States Patent Office Action for U.S. Appl. No. 12/344,164 dated Jun. 1, 2017 (15 pages).
United States Patent Office Action for U.S. Appl. No. 12/344,169 dated Feb. 20, 2015 (15 pages).
United States Patent Office Action for U.S. Appl. No. 12/344,169 dated Oct. 19, 2015 (18 pages).
United States Patent Office Action for U.S. Appl. No. 12/344,169 dated Sep. 8, 2016 (27 pages).
United States Patent Office Action for U.S. Appl. No. 12/344,169 dated May 16, 2017 (15 pages).
United States Patent Office Action for U.S. Appl. No. 12/784,487 dated Jan. 13, 2015 (18 pages).
United States Patent Office Action for U.S. Appl. No. 12/784,487 dated Oct. 23, 2015 (27 pages).
United States Patent Office Action for U.S. Appl. No. 12/784,487 dated Sep. 20, 2016 (25 pages).
United States Patent Office Action for U.S. Appl. No. 12/784,487 dated May 19, 2017 (14 pages).
United States Patent Office Action for U.S. Appl. No. 14/355,201 dated Sep. 2, 2016 (7 pages).
United States Patent Office Notice of Allowance for U.S. Appl. No. 14/355,201 dated Mar. 21, 2017 (8 pages).

* cited by examiner

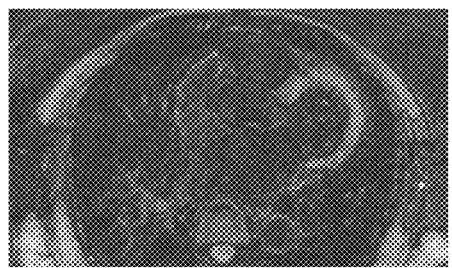 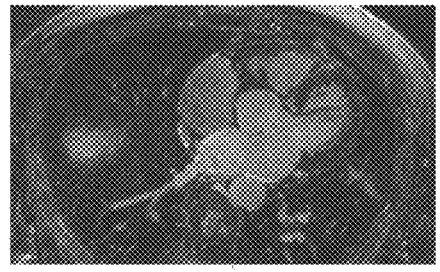
Fig. 3A Fig. 3B
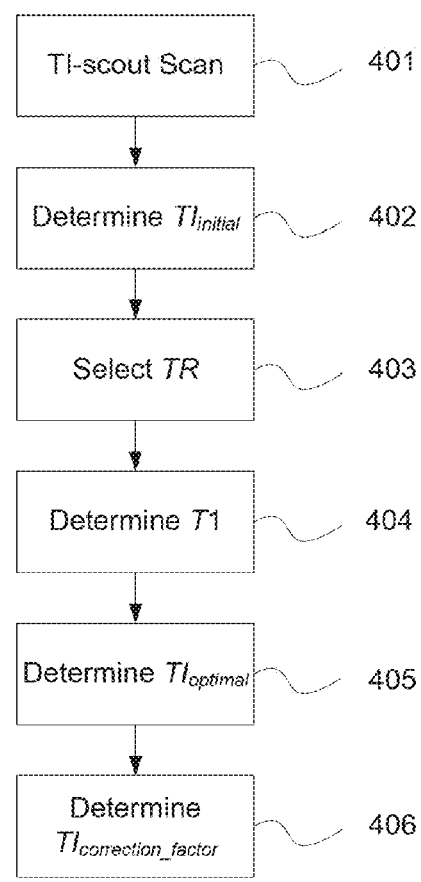
Fig. 4

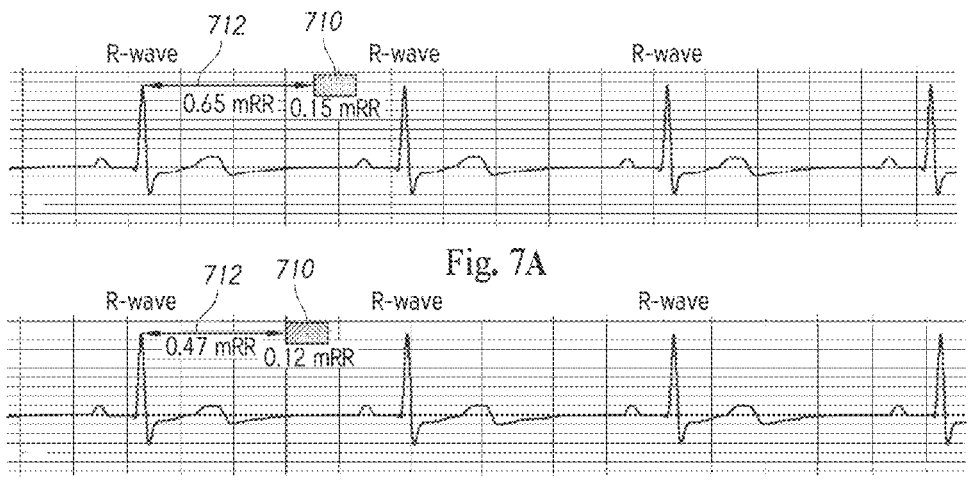
Fig. 7A
Fig. 7B
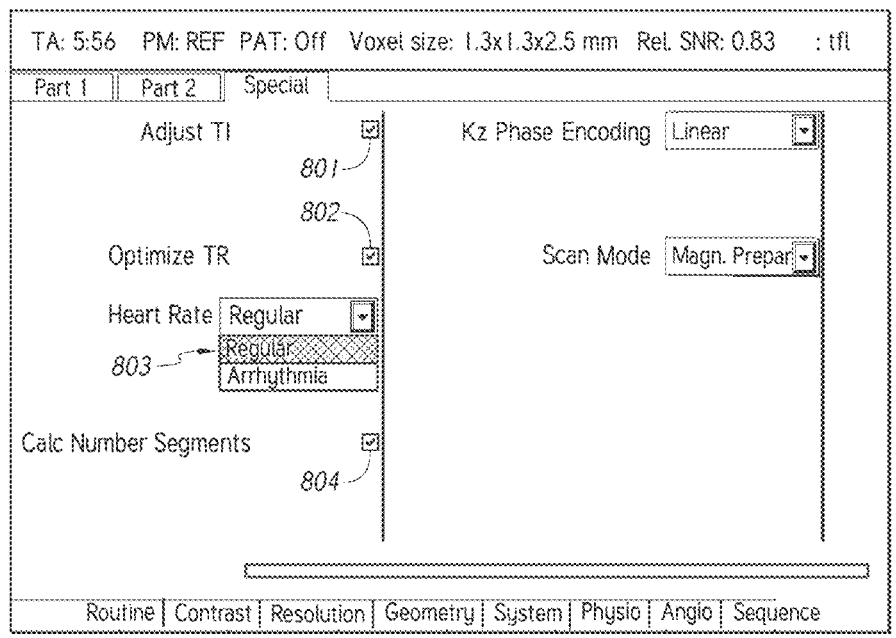
Fig. 8

PATIENT SPECIFIC SCAN PARAMETERS FOR MRI SCANNING

CROSS-REFERENCE TO RELATED APPLICATIONS

This application is a continuation of U.S. patent application Ser. No. 14/355,201, filed on Apr. 29, 2014, now U.S. Pat. No. 9,713,436, which is a national stage entry filed under 35 U.S.C. § 371, of International Application No. PCT/US2012/062616, filed on Oct. 30, 2012, which claims the benefit of U.S. Provisional Patent Application No. 61/553,836, filed on Oct. 31, 2011. The contents of these applications are incorporated herein by reference in their entireties.

BACKGROUND OF THE INVENTION

Atrial fibrillation (AF) has become one of the most common cardiac rhythm disturbances affecting millions of people in the United States. Progression of AF may be related to changes in atrial structure and function. Atrial remodeling, with subsequent alteration of LA structural components, may create a favorable substrate for sustaining AF. Currently, invasive tools such as electro-anatomical mapping using cardiac catheters have been developed for imaging and treating AF.

SUMMARY OF THE INVENTION

The subject technology is illustrated, for example, according to various aspects described below. Various examples of aspects of the subject technology are described. These are provided as examples, and do not limit the subject technology. It is noted that any of the these examples may be combined in any combination, and placed into a respective independent example.

The subject technology can, in some embodiments, dramatically improve the likelihood of obtaining late gadolinium enhancement magnetic resonance imaging (LGE-MRI) images with clinically acceptable quality. Existing pulse sequences for LGE-MRI of the left atrium give clinically acceptable image quality in about 50% cases. Using pulse sequences based on automatic calculation of patient specific scan parameters according to certain embodiments disclosed herein can achieve acceptable image quality in about 90% cases.

In one aspect, at least one cardiac MRI TI scout scan can be performed by applying an inversion pulse every predetermined heart beat of a patient. A first initial value of an inversion time $TI_{initial}$ is determined by assessing a set of image data generated from the scout scan. A first multiple of a duration between successive indicia of ventricular depolarization is selected, and a relaxation time T1 is determined based on the $TI_{initial}$ and the first multiple of the duration. A first optimized inversion time $TI_{optimal}$ is determined based on the relaxation time T1 and a second multiple of a duration between successive indicia of ventricular depolarization.

Based on the optimized inversion time $TI_{optimal}$ and the $TI_{initial}$, a correction factor that converts a second initial value of inversion time $TI_{initial}*$ to a second optimized inversion time $TI_{optimal}*$ can be determined. The correction factor can be determined by subtracting the $TI_{optimal}$ from the $TI_{initial}$. The $TI_{initial}$ can be equal to or different from the $TI_{initial}*$.

In some embodiments, the cardiac MRI scout scan comprises a late contrast enhancement magnetic resonance imaging (LE-MRI) performed on the left atrium of the patient. The inversion pulse may be applied every second or third heart beat of the patient. The first initial value of the inversion time $TI_{initial}$ may correspond to minimal intensity of the images of left ventricle. The relaxation time T1 may be calculated by an iterative algorithm of:

$$T1_{n+1} = TI_{initial} \frac{1}{\ln(2) - \ln(1 + e^{-TR/T1n})},$$

wherein n is a prescribed number of iteration starting from 0 until convergence, and TR equals to the first multiple of the duration between successive indicia. The first multiple may be 2 or 3, and the relaxation time may converge when n equals to 5. The optimized inversion time may be calculated by the relationship of:

$$TI_{optimal} = T1 \cdot \ln\left(\frac{2}{1 + e^{-TR/T1}}\right),$$

wherein TR is the second multiple. The second multiple may be 1. In some embodiments, the indicia comprise adjacent R-waves.

In some embodiments, an automatic position of data acquisition window in a stationary phase of cardiac cycle for left atrium may be activated, and a duration and position of data acquisition window may be determined according to heart rate of the patient. A number of k-space readouts per heart beat for the patient can be determined.

The subject technology further provides a device comprising a processing module configured to determine by a processor a relaxation time T1 based on (a) a first initial value of an inversion time $TI_{initial}$ obtained by performing an TI scout scan on a subject by an MRI device and (b) a first multiple of a duration between successive indicia of ventricular depolarization in an ECG signal in response to the TI scout scan, and determine a first optimal inversion time $TI_{optimal}$ based on the relaxation time T1 and a second multiple of a duration of successive indicia of ventricular depolarization of the ECG signal. The processing module is further configured to determine, based on the first optimized inversion time $TI_{optimal}$ and the first initial value of the inversion time $TI_{initial}$, a correction factor that converts a second initial value of inversion time $TI_{initial}*$ to a second optimized inversion time $TI_{optimal}*$. The correction factor can be determined by subtracting the $TI_{optimal}$ from the $TI_{initial}$. The $TI_{initial}$ can be equal to or different from the $TI_{initial}*$. The MRI device may include a late contrast enhancement magnetic resonance imaging (LE-MRI) performed on the left atrium of patient. The processing module can be further configured to apply the inversion pulse every second or third heart beat of the patient. The processing module can further be configured to determine the first initial value of inversion time $TI_{initial}$ that corresponds to minimal intensity of the images of left ventricle. The processing module can also be configured to calculate the relaxation time T1 by an iterative algorithm of:

$$T1_{n+1} = TI_{initial} \frac{1}{\ln(2) - \ln(1 + e^{-TR/T1n})},$$

wherein n is a prescribed number of iteration starting from 0 until convergence, and TR equals to the first multiple of the duration between successive indicia. The first multiple can be 2 or 3. The relaxation time may converge when n equals to 5.

The processing module is further configured to determine the first optimized inversion time by the relationship of:

$$TI_{optimal} = T1 \cdot \ln\left(\frac{2}{1+e^{-TR/T1}}\right),$$

wherein TR is the second multiple of the duration between successive indicia. In some embodiments, the second multiple is 1. The indicia may comprise adjacent R-waves.

In some embodiments, the processing module can be further configured to activate automatic position of data acquisition window in a stationary phase of cardiac cycle for left atrium, determine duration and position of data acquisition window according to heart rate of the subject, and determine a number of k-space readouts per heart beat for the subject.

In some embodiments, a non-transitory computer-readable storage medium having stored thereon a computer program comprising instructions that, when executed by at least one processor, operate to determine a first optimal inversion time $TI_{optima}$. The computer-readable storage medium comprise instructions for determining a relaxation time T1 based on (a) a first initial value of an inversion time $TI_{initial}$ obtained by performing an TI scout scan on a subject by an MRI device and (b) a first multiple of a duration between successive indicia of ventricular depolarization in an ECG signal in response to the TI scout scan. The computer-readable storage medium also comprise instructions for determining a first optimal inversion time $TI_{optimal}$ based on the relaxation time T1 and a second multiple of a duration of successive indicia of ventricular depolarization of the ECG signal.

The computer-readable storage medium further comprises instructions to determine, based on the first optimized inversion time $TI_{optimal}$ and the initial value of the inversion time $TI_{initial}$, a correction factor that converts a second initial value of inversion time $TI_{initial}^*$ to a second optimized inversion time $TI_{optimal}^*$. The correction factor can be determined by subtracting the $TI_{optimal}$ from the $TI_{initial}$. The $TI_{initial}$ can be equal to or different from the $TI_{initial}^*$. The computer-readable storage medium may further comprise instructions including any of applying the inversion pulse every second or third heart beat of the subject, determining the initial value of inversion time $TI_{initial}$ that corresponds to minimal intensity of the images of left ventricle, and calculating the relaxation time T1 by an iterative algorithm of:

$$T1_{n+1} = TI_{initial} \frac{1}{\ln(2) - \ln(1+e^{-TR/T1n})},$$

wherein n is a prescribed number of iteration starting from 0 until convergence, and TR equals to the first multiple of the duration between successive indicia. In some embodiments, the first multiple is 2 or 3. The relaxation time may converge when n equals to 5. The computer-readable storage medium further may further comprise instructions to determine the optimized inversion time by the relationship of:

$$TI_{optimal} = T1 \cdot \ln\left(\frac{2}{1+e^{-TR/T1}}\right),$$

wherein TR is the second multiple of the duration between successive indicia. The second multiple may be 1. The indicia may comprise adjacent R-waves.

In some embodiments, the non-transitory computer-readable medium may further comprise instructions for activating automatic position of data acquisition window in a stationary phase of cardiac cycle for left atrium, determining duration and position of data acquisition window according to heart rate of the subject, and determining a number of k-space readouts per heart beat for the patient.

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses can be combined in any combination, and placed into a respective independent clause, e.g., clause 1, clause 16, or clause 31. The other clauses can be presented in a similar manner.

1. A method comprising:
performing at least one cardiac MRI TI scout scan by applying an inversion pulse at a selected heart beat interval of a patient;
determining a first initial value of inversion time $TI_{initial}$ by assessing a set of image data generated from the scout scan;
selecting a first multiple of a duration between successive indicia of ventricular depolarization;
determining a relaxation time T1 based on the $TI_{initial}$ and the first multiple of the duration; and
determining a first optimized inversion time $TI_{optimal}$ based on the relaxation time T1 and a second multiple of a duration between successive indicia of ventricular depolarization.

2. The method of clause 1, further comprising determining, based on the $TI_{optimal}$ and the $TI_{initial}$, a correction factor that converts a second initial value of inversion time $TI_{initial}^*$ to a second optimized inversion time $TI_{optimal}^*$.

3. The method of clause 2, further comprising determining the correction factor by subtracting the $TI_{optimal}$ from the $TI_{initial}$.

4. The method of clause 2, wherein $TI_{initial}$ is equal to the $TI_{initial}^*$.

5. The method of clause 2, wherein $TI_{initial}$ is different from the $TI_{initial}^*$.

6. The method of clause 1, wherein the cardiac MRI scout scan comprises a late contrast enhancement magnetic resonance imaging (LE-MRI) performed on the left atrium of the patient.

7. The method of clause 1, wherein the inversion pulse is applied every second or third heart beat of the patient.

8. The method of clause 1, wherein the first initial value of the inversion time $TI_{initial}$ corresponds to minimal intensity of the images of left ventricle.

9. The method of clause 1, further comprising calculating the relaxation time T1 by an iterative algorithm of:

$$T1_{n+1} = TI_{initial} \frac{1}{\ln(2) - \ln(1+e^{-TR/T1n})},$$

wherein n is a prescribed number of iterations starting from 0 until convergence, and TR equals to the first multiple of the duration between successive indicia.

10. The method of clause 9, wherein the first multiple is between 2 to 3.

11. The method of clause 9, wherein the relaxation time converges when n equals to 5.

12. The method of clause 9, wherein the first optimized inversion time is calculated by the relationship of:

$$TI_{optimal} = T1 \cdot \ln\left(\frac{2}{1 + e^{-TR/T1}}\right),$$

wherein TR is the second multiple.

13. The method of clause 12, wherein the second multiple is 1.

14. The method of clause 1, wherein the indicia comprise adjacent R-waves.

15. The method of clause 1, further comprising:
activating automatic position of data acquisition window in a stationary phase of cardiac cycle for left atrium;
determining duration and position of data acquisition window according to heart rate of the patient; and
determining a number of k-space readouts per heart beat for the patient.

16. A device, comprising:
a processing module, configured to:
determine by a processor a relaxation time T1 based on (a) a first initial value of inversion time $TI_{initial}$ obtained by performing an TI scout scan on a subject by an MRI device and (b) a first multiple of a duration between successive indicia of ventricular depolarization in an ECG signal in response to the TI scout scan; and
determine a first optimal inversion time $TI_{optimal}$ based on the relaxation time T1 and a second multiple of a duration of successive indicia of ventricular depolarization of the ECG signal.

17. The device of clause 16, wherein the processor is further configured to determine, based on the first optimized inversion time $TI_{optimal}$ and the first initial value of the inversion time $TI_{initial}$, a correction factor that converts a second initial value of inversion time $TI_{initial}*$ to a second optimized inversion time $TI_{optimal}*$.

18. The device of clause 17, wherein the processor is further configured to determine the correction factor by subtracting the $TI_{optimal}$ from the $TI_{initial}$.

19. The device of clause 17, wherein $TI_{initial}$ is equal to $TI_{initial}*$.

20. The device of clause 17, wherein $TI_{initial}$ is different from $TI_{initial}*$.

21. The device of clause 16, wherein the MRI device includes a late contrast enhancement magnetic resonance imaging (LE-MRI) performed on the left atrium of the subject.

22. The device of clause 16, wherein the processing module is further configured to apply the inversion pulse every second or third heart beat of the subject.

23. The device of clause 16, wherein the processing module is further configured to determine the first initial value of inversion time $TI_{initial}$ that corresponds to minimal intensity of the images of left ventricle.

24. The device of clause 16, wherein the processing module is further configured to calculate the relaxation time T1 by an iterative algorithm of:

$$T1_{n+1} = TI_{initial} \frac{1}{\ln(2) - \ln(1 + e^{-TR/T1n})},$$

wherein n is a prescribed number of iteration starting from 0 until convergence, and TR equals to the first multiple of the duration between successive indicia.

25. The device of clause 24, wherein the first multiple is between 2 to 3.

26. The device of clause 24, wherein the relaxation time converges when n equals to 5.

27. The device of clause 24, wherein the processing module is further configured to determine the first optimized inversion time by the relationship of:

$$TI_{optimal} = T1 \cdot \ln\left(\frac{2}{1 + e^{-TR/T1}}\right),$$

wherein TR is the second multiple of the duration between successive indicia.

28. The device of clause 27, wherein the second multiple is 1.

29. The device of clause 16, wherein the indicia comprise adjacent R-waves.

30. The device of clause 16, wherein the processing module is further configured to:
activate automatic position of data acquisition window in a stationary phase of cardiac cycle for left atrium;
determine duration and position of data acquisition window according to heart rate of the subject; and
determine a number of k-space readouts per heart beat for the subject.

31. A non-transitory computer-readable storage medium having stored thereon a computer program comprising instructions, which when executed by at least one processor, operate to determine a first optimal inversion time $TI_{optimal}$, the computer-readable storage medium comprising:
instructions for determining a relaxation time T1 based on a first initial value of inversion time $TI_{initial}$ obtained by performing an TI scout scan on a subject by an MRI device and a first multiple of a duration between successive indicia of ventricular depolarization in an ECG signal in response to the TI scout scan; and
instructions for determining a first optimal inversion time $TI_{optimal}$ based on the relaxation time T1 and a second multiple of a duration of successive indicia of ventricular depolarization of the ECG signal.

32. The computer-readable storage medium of clause 31, further comprising instructions to determine, based on the $TI_{optimal}$ and the $TI_{initial}$, a correction factor that converts a second initial value of inversion time $TI_{initial}*$ to a second optimized inversion time $TI_{optimal}*$.

33. The computer-readable storage medium of clause 32, further comprising instructions to determine the correction factor by subtracting $TI_{optimal}$ from $TI_{initial}$.

34. The computer-readable storage medium of clause 32, wherein $TI_{initial}$ is equal to $TI_{initial}*$.

35. The computer-readable storage medium of clause 32, wherein $TI_{initial}$ is different from $TI_{initial}*$.

36. The computer-readable storage medium of clause 31, further comprising instructions to apply the inversion pulse every second or third heart beat of the subject.

37. The computer-readable storage medium of clause 31, further comprising instructions to determine the first initial value of inversion time $TI_{initial}$ that corresponds to minimal intensity of the images of left ventricle.

38. The computer-readable storage medium of clause 31, further comprising instructions to calculate the relaxation time T1 by an iterative algorithm of:

$$T1_{n+1} = TI_{initial} \frac{1}{\ln(2) - \ln(1 + e^{-TR/T1n})},$$

wherein n is a prescribed number of iteration starting from 0 until convergence, and TR equals to the first multiple of the duration between successive indicia.

39. The computer-readable storage medium of clause 38, wherein the first multiple is between 2 to 3.

40. The computer-readable storage medium of clause 38, wherein the relaxation time converges when n equals to 5.

41. The computer-readable storage medium of clause 38, wherein further comprising instructions to determine the first optimized inversion time by the relationship of:

$$TI_{optimal} = T1 \cdot \ln\left(\frac{2}{1 + e^{-TR/T1}}\right),$$

wherein TR is the second multiple of the duration between successive indicia.

42. The computer-readable storage medium of clause 41, wherein the second multiple is 1.

43. The computer-readable storage medium of clause 41, wherein the indicia comprise adjacent R-waves.

44. The non-transitory computer-readable storage medium of clause 31, further comprising instructions for:

activating automatic position of data acquisition window in a stationary phase of cardiac cycle for left atrium;

determining duration and position of data acquisition window according to heart rate of the subject; and determine a number of k-space readouts per heart beat for the patient.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

It is to be understood that both the foregoing general description and the following detailed description are exemplary and explanatory and are intended to provide further explanation of the subject technology as claimed.

BRIEF DESCRIPTION OF THE DRAWINGS

The accompanying drawings, which are included to provide further understanding of the subject technology and are incorporated in and constitute a part of this specification, illustrate aspects of the subject technology and together with the description serve to explain the principles of the subject technology.

FIG. 3A illustrates an image from high-resolution LGE-MRI of the left atrium when the inversion time TI is smaller than an optimal value.

FIG. 3B illustrates an image from high-resolution of LGE-MRI of the left atrium when the inversion time TI has an optimal value.

FIG. 4 shows a method for optimizing scan parameters for LGE-MRI of the left atrium.

FIG. 7A shows the position and duration of a data acquisition window for high-resolution LGE-MRI for patients with regular heart beats.

FIG. 7B shows the position and duration of a data acquisition window for high-resolution LGE-MRI for patients with irregular heart beats.

FIG. 8 illustrates an embodiment of a user interface that can be used in an exemplary process for realization of optimal k-space readouts.

DETAILED DESCRIPTION

In the following detailed description, numerous specific details are set forth to provide a full understanding of the subject technology. It will be apparent, however, to one of ordinarily skilled in the art that the subject technology may be practiced without some of these specific details. In other instances, well-known structures and techniques have not been shown in detail so as not to obscure the subject technology.

Late contrast enhancement magnetic resonance imaging (LE-MRI) such as high resolution, late gadolinium MRI (LGE-MRI) of the left atrium can be used as a technique to evaluate structural changes in the left atrium (LA) wall such as fibrosis caused by atrial fibrillation. LGE-MRI can also be used to detect scarring of the LA wall caused by interventional procedures used to treat AF, for example, radiofrequency (RF) ablation, cryoablation, and similar procedures. Success of RF ablation procedures strongly correlates with the degree of LA remodeling detected by LGE-MRI. The risk of stroke in AF patients may be associated with the degree of left atrial structural remodeling estimated by LGE-MRI. Scar maps of LA may be helpful in planning and performing repeat ablation procedures. Accuracy of fibrosis/scar evaluation may be strongly dependent on quality of LGE-MRI of the left atrium. Although the subject technology is described herein with reference to LGE-MRI, the subject technology is not limited to LGE-MRI. The subject technology can be applied to other contrast enhanced MRI besides gadolinium-enhanced MRI.

Figure 1:
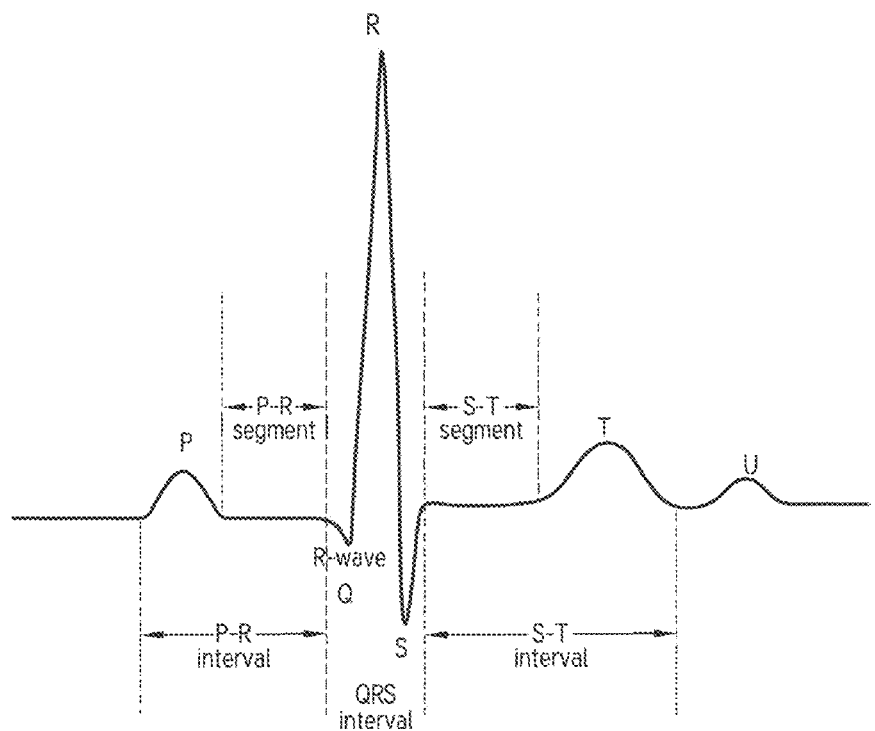
FIG. 1 shows a typical one-cycle ECG trace.

FIG. 1 illustrates a typical one-cycle electrocardiogram (ECG) signal/trace. The ECG is a system of recording bioelectric currents generated by the heart. Clinicians use the ECG to evaluate the condition of a patient's heart and perform further diagnosis. An ECG tracing is obtained by sampling bioelectric currents sensed by several electrodes, known as leads. The electrocardiogram (ECG) is a time-varying signal reflecting the ionic current flow which causes the cardiac muscles to contract and relax. A surface ECG is obtained by recording the potential difference between two electrodes placed on the surface of the skin. A single normal cycle of the ECG represents the successive atrial depolarization/repolarization and ventricular depolarization/repolarization which occurs with each heart beat. These are approximately associated with the peaks and troughs of the ECG waveform as shown in FIG. 1. A typical ECG tracing of a normal heartbeat (or cardiac cycle) consists of a P wave, a QRS interval and a T-wave. A small U wave is normally visible in 50 to 75% of ECGs. The baseline voltage of the electrocardiogram is known as the isoelectric line, measured as the portion of the ECG tracing following the T-wave and preceding the next P wave.

During normal atrial depolarization, the main electrical vector spreads from the right atrium to the left atrium. This is identified as the P wave on the ECG. The QRS interval corresponds to the depolarization of the ventricles. Because the ventricles contain more muscle mass than the atria, the QRS interval is larger than the P wave. In addition, the QRS interval tends to look "spiked" rather than rounded due to the increase in conduction velocity. A normal QRS interval is 0.06 to 0.10 sec (60 to 100 ms) in duration, but any abnormality of conduction takes longer, and causes widened QRS intervals. The PR interval is measured from the beginning of the P wave to the beginning of the QRS interval, usually 120 to 200 ms in duration. When a Q-wave is measured with an ECG, the PR interval may be called the PQ interval instead. The ST segment connects the QRS interval and the T-wave and has a duration of 0.08 to 0.12 sec (80 to 120 ms). The ST segment starts at the end of the QRS interval and ends at the beginning of the T-wave. However, since it is usually difficult to determine exactly where the ST segment ends and the T-wave begins, the relationship between the ST segment and T-wave should be examined together (ST interval). The typical ST segment duration is usually around 0.08 sec (80 ms). It should be essentially level with the PR segment. The T-wave represents the repolarization (or recovery) of the ventricles. The interval from the beginning of the QRS interval to the apex of the T-wave is referred to as the absolute refractory period. The last half of the T-wave is referred to as the relative refractory period (or vulnerable period).

Figure 2:
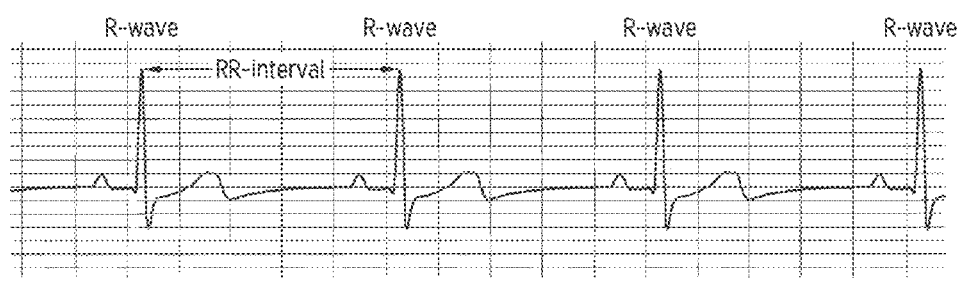
FIG. 2 illustrates the RR-interval between adjacent R-waves of an electrical cardiogram (ECG) signal.

Extracting useful clinical information from the real (noisy) ECG requires reliable signal processing systems. Conventional systems include R-peak detection, QT-interval detection and the derivation of heart rate and respiration rate from the ECG. The RR-interval is the time between successive R-peaks, the inverse of this time interval gives the instantaneous heart rate. A series of RR-intervals is known as a RR tachogram and variability of these RR-intervals reveals important information about the physiological state of the subject. FIG. 2 illustrates the RR-interval between adjacent R-waves of an electrical cardiogram (ECG) signal.

The image quality of high resolution LGE-MRI of the left atrium can be dependent on the choice of scan parameters such as inversion time (TI), the number of k-space readouts acquired per heart beat (Nseg) and the position of data acquisition window with respect to the R-wave of an electrocardiogram (ECG) signal. FIG. 3 illustrates images from high-resolution LGE-MRI of the left atrium illustrating contrast between fibrotic/scar tissue of LA wall and normal myocardium. The contrast between fibrotic/scar tissue of LA wall and normal myocardium, blood, and fat in LGE-MRI of the left atrium may be dependent on value of TI parameter. To control the contrast between healthy and abnormal or damaged tissue, the inversion recovery (IR) magnetization method is used in the MR sequences for imaging. In the inversion recovery sequence, the contrast between healthy and damaged, or undernourished tissue predominantly depends on longitudinal relaxation time T1. In an inversion module activated before the actual imaging sequence, a preparation pulse, often a radio-frequency (RF) inversion (180°) pulse inverts the longitudinal magnetization. The transversal magnetization thereby remains equal to zero. During the subsequent repetition, the negative longitudinal magnetization decays to zero and then rises again. Since no transversal magnetization can be created, no signal is measured either. In order to be able to generate a magnetic resonance signal, the longitudinal magnetization must be converted into a transversal magnetization via a subsequent excitation pulse, for example, a 90° excitation pulse. One measurement parameter in this sequence is the point in time between the inversion pulse and the excitation pulse called the inversion time TI. The contrast between different tissue types is set with the inversion time TI. Usually, TI value for cardiac LGE-MRI scan is found using TI scout scan based on the well known Look-Locker technique. A default set of scan parameters for all patients is used without taking into account that a patient may be in sinus rhythm or arrhythmia and may have a slow or fast heart rate. Furthermore, the value of TI parameter found from TI scout scan may be suboptimal for LGE-MRI of the left atrium in many cases. Image quality of existing LGE-MRI pulse sequences may often be not clinically helpful because of blurring of left atrium wall and poor contrast between healthy and abnormal tissues of the left atrium. In such cases of poor image quality, LGE-MRI scans may typically be repeated. Repeated scans may have reduced contrast between fibrotic/scar tissue of LA and normal myocardium, fat, and blood due to contrast agent washout. To resolve this problem, additional injection of contrast agent may be administered or patient may rescheduled to be scanned on another date.

The scan parameters for high-resolution LGE-MRI of the left atrium can be optimized individually for each patient (i.e., be patient specific). This optimization can be performed automatically or with minimal MRI technologist interaction to minimize errors and speed up prescription of scan parameters. FIGS. 3A-3B indicate that the contrast between fibrotic/scar tissue of LA wall and normal myocardium is dependent on the prescribed TI value. For example, in FIG. 3A, the prescribed TI value was smaller than an optimal value. As a result, fibrotic tissue of LA wall has the same intensity as normal myocardium. Whereas, in FIG. 3B, the prescribed TI value for which had an optimal value, a high contrast between fibrotic tissue and normal myocardium is obvious.

Figure 5:
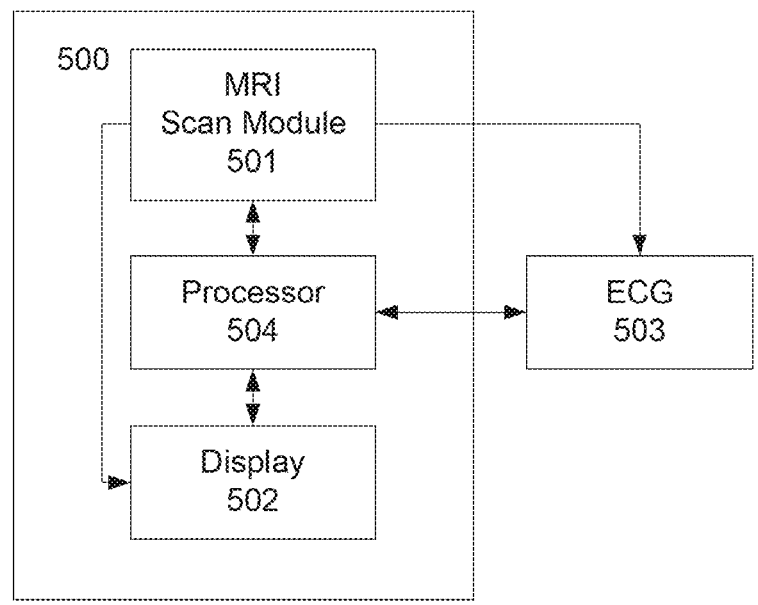
FIG. 5 shows an apparatus for optimizing scan parameters for LGE-MRI of the left atrium.

FIG. 4 shows an exemplary method for optimizing scan parameters for LGE-MRI of the left atrium, and FIG. 5 shows an exemplary device operative to optimize the scan parameters and for performing the LGE-MRI scan. In step 401, TI scout scans can be performed by an MRI device 500 as shown in FIG. 5, for example. To perform the scans, a radio frequency (RF) inversion pulse is applied to a scan module 501 at predetermined times, for example, every second or third heart beat. It is appreciated that the predetermined times can be selected heart beat intervals and may be adjusted according to the actual need and the actual physical condition of the patient. For example, the inversion RF pulse can be applied at every third heart beat when the patient has relatively fast heart rates such as faster than 90 beats per minutes (bpm). The inversion RF pulse can be applied at other selected heart beat intervals such as, for example, every fourth heart beat.

Figures 6A, 6B, 6C, 6D:
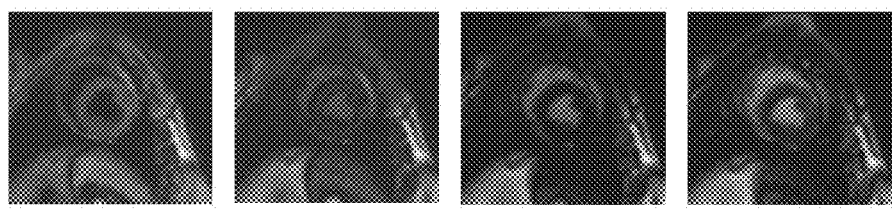
FIGS. 6A-6D show images from TI scout scan, with each imaging having a respective value of TI.

In response to the scout scan, MRI images are generated and can be output to a display 502, and an ECG signal similar to that as shown in FIG. 2 can be generated by the ECG 503. By visually inspecting a set of MRI images generated from the TI scout scan, an initial value of inversion time $TI_{initial}$ corresponding to minimal intensity of normal myocardium of the left ventricle may be determined in step 402. FIGS. 6A-6D show images from TI scout scans, with each scan having a respective TI value, for a patient. FIG. 6A has a TI value of 185 msec. FIG. 6B has a TI value of 245 msec. FIG. 6C has a TI value of 305 msec. FIG. 6D has a TI value of 365 msec. As shown, minimal intensity of myocardium of the left ventricle corresponds to TI=305 msec. In alternative or addition to visual inspection, a processor 504 (FIG. 5) may be used to automatically determine and output the initial value of inversion time $TI_{initial}$ based on the image data of the MRI scan module 501. In embodiments wherein visual inspection and automatic determination are both performed to determine an initial value of inversion time $TI_{initial}$ corresponding to minimal intensity of normal myocardium of the left ventricle, the automatically determined value can be presented for confirmation by visual inspection.

Based on the initial value of inversion time $TI_{initial}$ and a time interval between successive indicia of ventricular depolarization or adjacent inversion pulses TR, a relaxation time T1 for the normal myocardium can be calculated by an iterative algorithm:

$$T1_{n+1} = TI_{initial} \frac{1}{\ln(2) - \ln(1 + e^{-TR/T1n})} \quad (1)$$

In the above equation Eq. (1), n is a prescribed number of iteration between 0 and N. Depending on the TI scout protocol, TR may be input by the user through a user interface (not shown) or automatically selected by the processor 504 in step 403 according to the specific information and conditions of the patient input to the system through the user interface or transmitted from other devices. TR may equal to two or three times of the duration of successive indicia of ventricular depolarization, for example, two to three intervals of adjacent R-waves (2 RR or 3 RR). It is appreciated that the multiple of the indicia can be either an integer or a fraction. For initialization, n=0, and $TI_{n=0}=0$; and when n=1, $$T1_1 = TI_{initial} \frac{1}{\ln(2)}.$$

When the iterative algorithm converges, typically as fast as N=5 with an accuracy higher than 1%, the TI value can be obtained by the processor 504 in step 404.

In step 405, an optimum value for the TI parameter for LGE-MRI of the left ventricle can be calculated by the processor 504 from Eq. (2):

$$TI_{optimal} = T1 \cdot \ln\left(\frac{2}{1 + e^{-TR/T1}}\right) \quad (2)$$

In Eq (2), TR represents a multiple of a duration between successive indicia of ventricular depolarization or an interval between the adjacent inversion pulses in the LGE-MRI scan of the left atrium. The parameter TR may be the mean time interval between successive indicia of ventricular depolarization such as the interval between two adjacent R-waves (1 RR), as shown in FIG. 2. The MRI system may receive the values for the parameter TR from the ECG unit coupled to the MRI system. The ECG unit can be used to perform an ECG monitoring of a patient who is the subject of the LGE-MRI scan. The processor 504 can further compute a correction factor for the TI as follows:

$$TI_{CorrectionFactor} = TI_{initial} - TI_{optimal} \quad (3)$$

By proscribing the $TI_{optimal}$ value for LGE-MRI scan, an ECG trace can be obtained based on the actual conditions of the patient in concern. For the convenience of operation, instead of proscribing the $TI_{optimal}$, the MRI technologist can also read this value and prescribe TI value for LGE-MRI scan as TI value found from TI scout minus the correction factor. Alternatively, the data of $TI_{optimal}$ or $TI_{CorrectionFactor}$ can be automatically proscribed by the processor 504 for the MRI scan. For example, an RR value of 800 msec and $TI_{initial}$ value of 300 msec, respective values for T1, $TI_{optimal}$ and $TI_{CorrectionFactor}$ would be equal to 451.34, 242.02 and 57.98 msec.

As discussed above, image quality of high resolution LGE-MRI of the left atrium can also be dependent on the choice of the number of k-space readouts acquired per heart beat (Nseg) and the position of data acquisition window with respect to the R-wave of an ECG signal, k-space is a mathematical space in which the Fourier transform of the image is presented. The data acquired for MRI reconstruction generally correspond to samples of k-space. Typically, the more k-space readouts, the finer the images will be presented in addition to the k-space readouts. In addition, cardiac MRI scan typically requires synchronization of data acquisition with heart motion. Methods for such synchronization includes ECG gating, for example. For ECG gating, R-wave can be used as a reference point. Cardiac MRI sequences may acquire a subset of k-space data for every heart beat. Duration and position of data acquisition window relative to R-wave peak can determine scan time and visibility of cardiac structures. To accurately visualize small cardiac structures such as atrial wall (2-3 mm thick), a data acquisition window can be positioned in the stationary phase of cardiac cycle of the structure of interest. In addition, duration of the data acquisition window can be less than the duration of the stationary phase and large enough to keep scan time efficient at the same time.

To optimize imaging of the left atrium, images from cine cardiac MRI studies from multiple patients, for example, over 100 atrial fibrillation patients (as were assessed by the inventors), can be analyzed to detect positions and duration of the longest stationary phase of the cardiac cycle of the left atrium. Heart rate can be characterized by a mean RR-interval (mRR) and standard deviation of RR-interval (stdRR). Some empirical data obtained by the inventors show that, for patients with regular heart rate, for example, stdRR/mRR<0.05, duration of the stationary phase is about 20% of mRR, that is, 0.2 mRR, and the stationary phase is located from about 63%) to about 82% of mRR. For patients with non-regular heart rate, for example, stdRR/mRR>0.05, duration of the stationary phase is about 15% of mRR and the stationary phase is located from about 45% to about 60% of mRR. For patients with regular heart rate, the duration $T_{DAW}$ of data acquisition window 710 (FIG. 7A) is about 15% of mRR ($T_{DAW}$=0.15 mRR), and the data acquisition window is located from about 65% to about 80% of mRR. FIG. 7A illustrates the duration of the data acquisition window 710 and the time 712 between the peak of an R-wave and initiation of the data acquisition window. For patients with irregular heart rate, duration $T_{DAW}$ of data acquisition window 710 is reduced to about 12% of mRR, which is positioned about 0.47 mRR to about 0.59 mRR as shown in FIG. 7B. More specifically, a patient with regular heart rate of 60 beats per minute (mRR=1000 msec), $T_{DAW}$ is about 150 msec, and data acquisition starts from, for example, 650 msce after peak of R-wave. The start of data acquisition can be measured from the peak of an R-wave in some embodiments. In some embodiments, the start of data acquisition can be measured from another part of an ECG.

FIG. 8 illustrates an embodiment of a user interface that can be used in an exemplary process for realization of optimal number of k-space readouts per cardiac cycle. The display layout can include elements 801, 802, 803, 804 for receiving inputs from a user. The elements for receiving user input can comprise, for example, check boxes, selection menus, radio buttons, or a combination thereof. A box 801 can be selected to instruct the system to calculate the $TI_{correction\_factor}$ such as by the process shown in FIG. 4, for example. In some embodiments, selecting the box 801 can also instruct the system to apply the calculated $TI_{correction\_factor}$. A box 802 can be selected to instruct the system to automatically position the data acquisition window in stationary phase of the cardiac cycle for left atrium. A menu 803 can receive an input indicating whether the heart rate of a patient is regular or arrhythmic. A box 804 can be checked to instruct the system to calculate the optimal number of k-space readouts per cardiac cycle. Calculation of duration of the data acquisition window and the position of the data acquisition window relative to R-wave can be implemented in the pulse sequence for high-resolution LGE-MRI of the left atrium. Thus, in the embodiment illustrated in FIG. 8, a user can instruct the system to automatically perform some or all of the presented actions while the MRI technologist only needs to choose whether the patient's heart rate is regular or arrhythmic. Such step can easily be implemented automatically too. Whether the patient's heart rate is regular or arrhythmic can be determined from the values of mRR and stdRR that are known in pulse sequence. Thus, whether patient has regular or non-regular (arrhythmic) heart rate can be decided automatically by the system. The boxes can be checked to instruct automatic performance of actions as described above with reference to FIG. 8, or the actions can be performed by default. In embodiments wherein the actions are performed by default, checking of a box can provide an instruction not to perform particular actions automatically.

The number of k-space readouts can be acquired every heart beat from $$N_{seg} = \frac{T_{DAW}}{T_{readout}} \quad (4)$$

In Eq. (4), $T_{readout}$ is a duration of one k-space readout. For patients with a regular heart rate, the number of k-space readout $N_{seg}$ is 0.15 mRR/$T_{readout}$. For patients with an irregular heart rate, the k-space readout N=seg is 0.12 mRR/$T_{readout}$. Therefore, when a patient has a regular heart rate of 60 beats per minute (mRR=1000 msec) and qj$T_{readout}$=3 msec, $N_{seg}$ is equal to 50. That is, 50 k-space readouts are performed for each heart beat. The calculation of $N_{seg}$ can be implemented in the pulse sequence for high-resolution LGE-MRI of the left atrium. The MRI technologist only needs to read this value and prescribe it in the corresponding step.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the invention have been described, these have been presented by way of example only, and are not intended to limit the scope of the invention. Indeed, the novel methods and systems described herein may be embodied in a variety of other forms without departing from the spirit thereof. The accompanying claims and their equivalents are intended to cover such forms or modifications as would fall within the scope and spirit of the invention.

What is claimed is:

1. A device for performing an MRI scan using patient specific scan parameters, the device comprising:
    a processor, configured to:
        determine a relaxation time T1 based on (a) a first initial value of inversion time $TI_{initial}$ obtained by performing a plurality of TI scout scans on a patient by an MRI device and (b) a first multiple of a duration between successive indicia of ventricular depolarization in an ECG signal in response to the plurality of TI scout scans,
        determine a first optimal inversion time $TI_{optimal}$ based on the relaxation time T1 and a second multiple of a duration of successive indicia of ventricular depolarization of the ECG signal,
        determine a correction factor for the inversion time that converts a second initial value of inversion time $TI_{initial}*$ to a second optimized inversion time $TI_{optimal}*$ by subtracting the $TI_{optimal}$ from the $TI_{initial}$, and
        generate an output to the MRI device causing the MRI device to perform an MRI scan based on the first optimized inversion time $TI_{optimal}$ and the correction factor.

2. The device of claim 1, wherein $TI_{initial}$ is equal to $TI_{initial}*$.

3. The device of claim 1, wherein $TI_{initial}$ is different from $TI_{initial}*$.

4. The device of claim 1, wherein the MRI device performs a late contrast enhancement magnetic resonance imaging (LE-MRI) scan on a left atrium of the patient.

5. The device of claim 1, wherein each scout scan includes applying an inversion pulse at a selected heart beat interval of the patient and applying an excitation pulse, and further wherein the processor is configured to generate an output to the MRI device causing the MRI device to apply the inversion pulse every second or third heart beat of the patient.

6. The device of claim 1, wherein the processor is further configured to determine the first initial value of the inversion time $TI_{initial}$ that corresponds to minimal intensity of the images of a left ventricle.

7. The device of claim 1, wherein the processor is further configured to calculate the relaxation time T1 by an iterative algorithm of:

$$T1_{n+1} = TI_{initial} \frac{1}{\ln(2) - \ln(1 + e^{-TR/T1n})},$$

wherein n is a prescribed number of iteration starting from 0 until convergence, and TR equals to the first multiple of the duration between successive indicia.

8. The device of claim 7, wherein the first multiple is between 2 to 3.

9. The device of claim 7, wherein the relaxation time converges when n equals to 5.

10. The device of claim 7, wherein the processor is further configured to determine the first optimized inversion time by the relationship of:

$$TI_{optimal} = T1 \cdot \ln\left(\frac{2}{1 + e^{-TR/T1}}\right),$$

wherein TR is the second multiple of the duration between successive indicia.

11. The device of claim 10, wherein the second multiple is 1.

12. The device of claim 1, wherein the indicia comprise adjacent R-waves.

13. A non-transitory computer-readable storage medium having stored thereon a computer program comprising instructions, which when executed by a processor, operate to determine a first optimal inversion time $TI_{optimal}$, the computer-readable storage medium comprising:
  instructions to determine a first initial value of inversion time $TI_{initial}$ by assessing a set of image data generated from a plurality of TI scout scans;
  instructions to select a first multiple of a duration between successive indicia of ventricular depolarization;
  instructions to determine a relaxation time T1 based on the first initial value of inversion time $TI_{initial}$ and the first multiple of the duration;
  instructions to determine a first optimized inversion time $TI_{optimal}$ based on the relaxation time T1 and a second multiple of a duration of successive indicia of ventricular depolarization; and
  instructions to perform an MRI scan using the first optimized inversion time $TI_{optimal}$.

14. The non-transitory computer-readable storage medium of claim 13, further comprising instructions to determine, based on the $TI_{optimal}$ and the $TI_{initial}$, a correction factor, instruction to convert a second initial value of inversion time $TI_{initial}*$ to a second optimized inversion time $TI_{optimal}*$ using the correction factor, and instructions to perform a second MRI scan using the second optimized inversion time $TI_{optimal}*$.

15. The non-transitory computer-readable storage medium of claim 14, further comprising instructions to determine the correction factor by subtracting the $TI_{optimal}$ from the $TI_{initial}$.

16. The non-transitory computer-readable storage medium of claim 14, wherein $TI_{initial}$ is equal to the $TI_{initial}*$.

17. The non-transitory computer-readable storage medium of claim 14, wherein $TI_{initial}$ is different from the $TI_{initial}*$.

18. The non-transitory computer-readable storage medium of claim 13, wherein each of the TI scout scans includes application of an inversion pulse at a selected heart beat interval of a patient and application of an excitation pulse, and further comprising instructions to apply the inversion pulse every second or third heartbeat of the patient.

19. The non-transitory computer-readable storage medium of claim 13, further comprising instructions to determine the first initial value of inversion time $TI_{initial}$ that corresponds to minimal intensity of the images of a left ventricle.

20. The non-transitory computer-readable storage medium of claim 13, further comprising instructions to calculate the relaxation time T1 by an iterative algorithm of:

$$T1_{n+1} = TI_{initial} \frac{1}{\ln(2) - \ln(1 + e^{-TR/T1n})},$$

wherein n is a prescribed number of iteration starting from 0 until convergence, and TR equals to the first multiple of the duration between successive indicia.

21. The non-transitory computer-readable storage medium of claim 20, wherein the first multiple is between 2 to 3.

22. The non-transitory computer-readable storage medium of claim 20, wherein the relaxation time converges when n equals to 5.

23. The non-transitory computer-readable storage medium of claim 20, wherein further comprising instructions to determine the first optimized inversion time by the relationship of:

$$TI_{optimal} = T1 \cdot \ln\left(\frac{2}{1 + e^{-TR/T1}}\right),$$

wherein TR is the second multiple of the duration between successive indicia.

24. The non-transitory computer-readable storage medium of claim 23, wherein the second multiple is 1.

25. The non-transitory computer-readable storage medium of claim 23, wherein the indicia comprise adjacent R-waves.

26. The non-transitory computer-readable storage medium of claim 13, further comprising instructions to:
  activate an automatic position of a data acquisition window in a stationary phase of a cardiac cycle for a left atrium;

determine a duration and a position of the data acquisition window according to a heart rate of the patient; and
determine a number of k-space readouts per heart beat for the patient.

\* \* \* \* \*